(12) United States Patent
Putnam

(10) Patent No.: US 6,793,659 B2
(45) Date of Patent: Sep. 21, 2004

(54) INTRAMEDULLARY ROD FOR WRIST FIXATION

(75) Inventor: Matthew D. Putnam, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/975,514

(22) Filed: Oct. 12, 2001

(65) Prior Publication Data

US 2003/0073999 A1 Apr. 17, 2003

(51) Int. Cl.$^7$ ............................................. A61B 17/56
(52) U.S. Cl. .......................... 606/62; 606/64; 606/69
(58) Field of Search ............................ 606/62, 64, 76, 606/102

(56) References Cited

U.S. PATENT DOCUMENTS

| | | | |
|---|---|---|---|
| 4,229,840 A | 10/1980 | Gristina | |
| 4,653,487 A | 3/1987 | Maale | |
| 4,846,162 A | * 7/1989 | Moehring | ..................... 606/67 |
| 5,100,405 A | 3/1992 | McLaren | |
| 5,197,966 A | 3/1993 | Sommerkamp | |
| 5,514,137 A | 5/1996 | Coutts | |
| 5,586,985 A | 12/1996 | Putnam et al. | |
| 5,683,389 A | 11/1997 | Orsak | |
| 5,718,704 A | 2/1998 | Medoff | |
| 5,779,703 A | 7/1998 | Benoist | |
| 5,779,705 A | * 7/1998 | Matthews | ..................... 606/67 |
| 5,935,127 A | * 8/1999 | Border | ......................... 606/62 |
| 5,979,658 A | * 11/1999 | Allen et al. | .................. 206/572 |
| 6,034,296 A | 3/2000 | Elvin et al. | |
| 6,059,789 A | 5/2000 | Dinger et al. | |
| 6,096,040 A | 8/2000 | Esser | |
| 6,106,528 A | * 8/2000 | Durham et al. | ............... 606/64 |
| 6,129,729 A | 10/2000 | Snyder | |
| 6,171,309 B1 | 1/2001 | Huebner | |
| 6,221,074 B1 | 4/2001 | Cole et al. | |
| 6,235,031 B1 | 5/2001 | Hodgeman et al. | |
| 6,270,499 B1 | 8/2001 | Leu et al. | |
| 2001/0049529 A1 | * 12/2001 | Cachia et al. | ................. 606/72 |

FOREIGN PATENT DOCUMENTS

| | | |
|---|---|---|
| EP | 0 547 380 A1 | 6/1993 |
| EP | 1 095 626 A1 | 5/2001 |
| WO | WO 00/67651 | 11/2000 |
| WO | WO 01/52772 | 7/2001 |
| WO | WO 02/24088 | 3/2002 |

OTHER PUBLICATIONS

O'Conner D.O. et al., "In vitro measurement of strain in the bone cement surrounding the femoral component of total hip replacements during simulated gait and stair–climbing," J. Orthop. Res. 14(5):769–777 (Sep. 1996).

Maloney, W.J. et al., "Biomechanical and histological investigation of cemented total hip arthroplasties. A study of autopsy–retrieved femurs after in vivo cycling," Clin. Orthop 249:129–140 (Dec. 1989).

Page, A.E. et al., "Determination of loading parameters in the canine hip in vivo," J. Biomech. 26(4–5):571–579 (Apr.–May 1993).

* cited by examiner

*Primary Examiner*—Cary E. O'Connor
*Assistant Examiner*—Candice C. Melson
(74) *Attorney, Agent, or Firm*—Fish & Richardson P.C., P.A.

(57) ABSTRACT

An intramedullary rod kit for fixation of a distal radius fracture includes an intramedullary rod. The intramedullary rod includes a diaphyseal segment including at least one first mounting section configured to receive a tensioning device, a middle segment, and a joint segment including at least one second mounting section configured to receive a tine. The diaphyseal segment, the middle segment, and the joint segment define a curved configuration that is substantially similar to a curvature of the intramedullary canal of a human radius.

124 Claims, 15 Drawing Sheets

GENERIC FRACTURE CLASSIFICATION DISTAL RADIUS (LAT) PATTERN      (PA VIEW)

TYPE A
EXTRA ARTICULAR

TYPE B
MARGINAL

TYPE C
INTRA ARTICULAR

INTRAMEDULLARY ROD FOR WRIST FIXATION

TECHNICAL FIELD

This invention relates to wrist fixation, and more particularly to an intramedullary rod for internal bridging wrist fixation.

BACKGROUND

As illustrated in FIG. 1, the wrist joint 10 is formed at the intersection of the radius 15 and the ulna 20 with the metacarpals 25 and the carpals 30. The radius 15 includes an intramedullary canal 33 that runs the length of the radius. The canal 33 has a variable cross-sectional shape and cross-sectional diameter over its length. For example, the canal is wider and more oval shaped near the wrist joint but becomes rounded and narrower in the mid-region of the radius.

The wrist joint 10 and associated bones can be damaged, for example, in a fall. As illustrated in FIGS. 2a–d, a frequent injury to the wrist joint 10 is a distal radius fracture 35 in which a distal portion 40 of the radius is fractured away from the radius. Inherent bony instability, soft tissue damage, and frequent associated injuries make distal radius fractures very difficult to treat. Treatment of the fracture includes placement of a T-plate and external fixation, such as a cast. The functional outcome of the wrist joint after the treatment is generally directly related to residual deformity, both extra-articular alignment and intra-articular step-off, in the joint. FIGS. 2b–d illustrate various types of injuries according to the OTA classification system. For example, FIG. 2b illustrates a Type A injury, which occurs when the fracture line is along the plane of the epiphyseal plate. FIG. 2c illustrates a Type B injury, which occurs when the fracture line is along the margin of the joint. FIG. 2d illustrates a Type C injury, which occurs when the fracture line is along the plane of the epiphyseal plate, but also extends into the joint.

SUMMARY

In one general aspect, an intramedullary rod kit for fixation of a distal radius fracture includes an intramedullary rod. The intramedullary rod includes a diaphyseal segment including at least one first mounting section configured to receive a tensioning device, a middle segment, and a joint segment including at least one second mounting section configured to receive a tine. The diaphyseal segment, the middle segment, and the joint segment define a curved configuration that is substantially similar to a curvature of the intramedullary canal of a human radius.

Implementation and embodiments of the intramedullary rod kit may include one or more of the following features. For example, the joint segment may include an opening into a longitudinal channel that extends along a portion of a length of the intramedullary rod. The longitudinal channel may include a threaded portion. The kit may further include a guide that is configured to be mounted to the intramedullary rod and configured to orient drill guides to be collinear with the first mounting section and the second mounting section of the intramedullary rod. The guide may be mounted to the intramedullary rod by insertion of a portion of the guide into the longitudinal channel in the intramedullary rod. The portion of the guide that is inserted into the longitudinal channel may be threadably inserted into the longitudinal channel.

An outer diameter of the intramedullary rod may vary between approximately 10 mm and 25 mm at the joint segment and approximately 2 mm and 9 mm at the diaphyseal segment. More particularly, the outer diameter of the intramedullary rod may vary between approximately 12 mm and 15 mm at the joint segment and approximately 3 mm and 5 mm at the diaphyseal segment. Even more particularly, the outer diameter of the intramedullary rod may vary between approximately 14 mm at the joint segment and approximately 3 mm at the diaphyseal segment.

The joint segment may have one of a round cross-section and an oval cross-section. The diaphyseal segment may have a round or a generally round cross-section. A length of the rod may be between approximately 50 mm and 100 mm, and more particularly, may be approximately 80 mm.

The first mounting section may include at least one channel having a threaded inner diameter and may further include at least one bone screw configured to be passed through the first mounting section to mount the intramedullary rod to a diaphyseal portion of the radius. The bone screw may be one of a unicortical bone screw and a bicortical bone screw.

The tine(s) may include a shaft and may be mounted to the rod in the second mounting section. The second mounting section may include a channel that includes a threaded portion and the tine may include a first non-threaded section and a second threaded section that is configured to be threadably mated to the threaded portion of the channel. The second channel may include a threaded portion and the tine may include a first threaded section and a second threaded section that is configured to be threadably mated to the threaded portion of the channel. The first threaded section may include threads that are configured to be threadably mated with the bone fragment or fragments.

The tine may include an insert from which at least one shaft extends and the insert may be configured to be mated to the second mounting section. The shaft may be integrally formed with the insert. The insert may include a channel that receives a screw and the intramedullary rod may include a threaded channel that also receives the screw. The opening in the intramedullary rod may further include an opening extending through the intramedullary rod and being configured to receive the shaft.

The intramedullary rod kit may further include a snap fit tine that includes a head having an opening into which teeth protrude and from which a tine extends, and the second channel mounting section may be configured as a channel around at least a portion of the circumference of the intramedullary rod and from which teeth protrude, and the head may be configured to be mated with the second mounting section.

The intramedullary rod kit may further include a tensiometer mounted to one or more of the intramedullary rod and the tine and being configured to measure a tension exerted against one or both of the intramedullary rod and the tine. The kit then may include a transmitter for transmitting the measured tension and a receiver for receiving and displaying the measured tension. The intramedullary rod kit may further include written instructions for use, an instructional video, and a drill bit configured to drill a hole in bone tissue.

The tensioning device may be a tie band fastener including a tie band, a slidable tab, and a stop. The tensioning device also may be a molly bolt system that includes a head, a nut, and one or more flexible arms extending between the head and the nut.

The intramedullary rod, the tensioning device, and/or the tine may be coated with a therapeutic agent. The diaphyseal segment of the intramedullary rod may have a dimpled surface.

The details of one or more embodiments of the intramedullary rod and the ancillary and accessory articles are set forth in the accompanying drawings and the description below. Other features and advantages of the intramedullary rod and the ancillary and accessory articles will be apparent from the description, the drawings, and the claims.

DESCRIPTION OF DRAWINGS

Like reference symbols in the various drawings indicate like elements.

DETAILED DESCRIPTION

Figure 1:
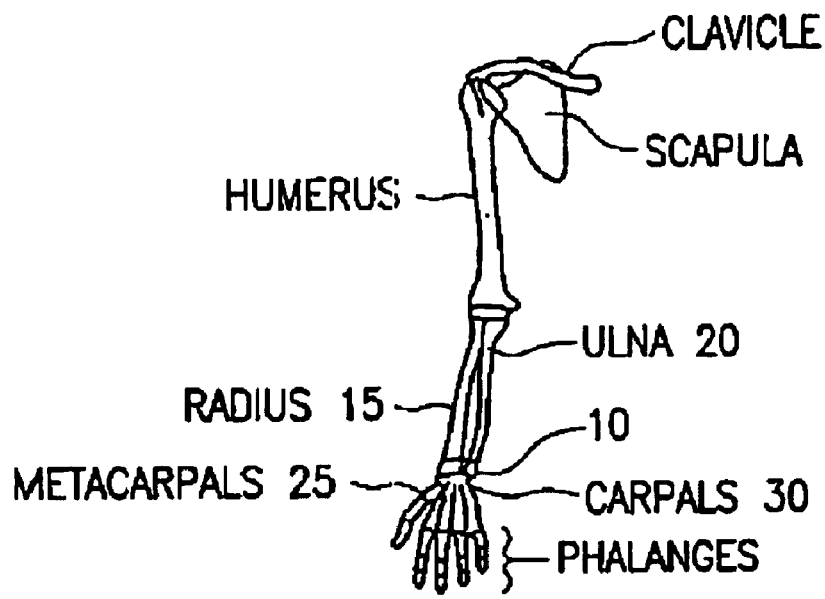
FIG. 1 is a front view of the anatomy of a human arm.
Figure 2A:
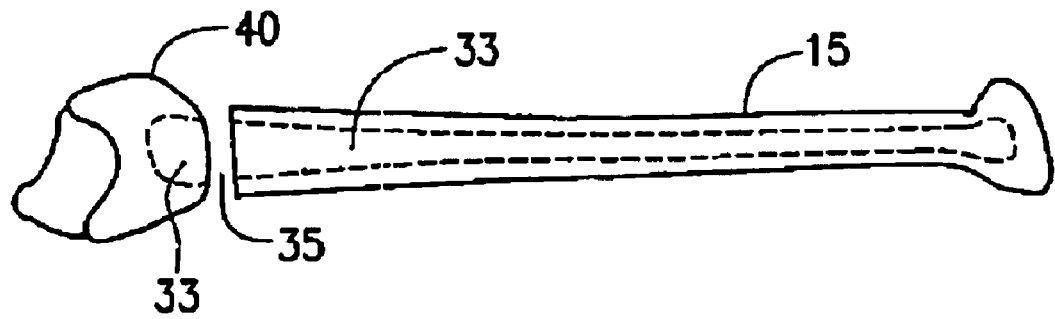
FIG. 2a is a side view of a distal radius fracture.
Figure 2B:
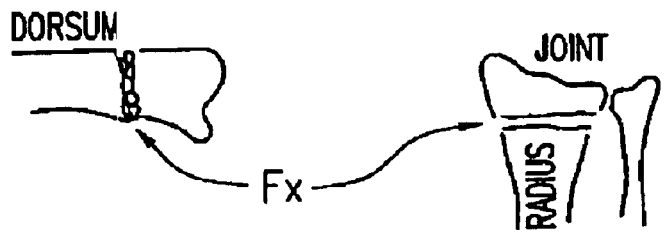
FIGS. 2b–d are side views of different types of distal radius fractures classified according to the OTA classification system.
Figure 2C:
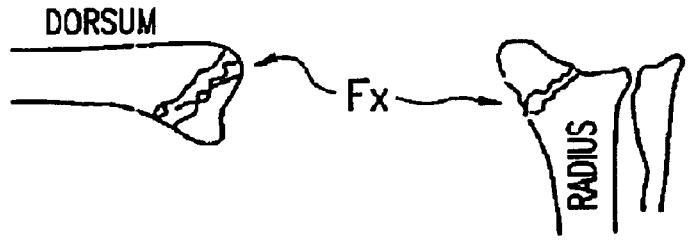
Figure 2D:
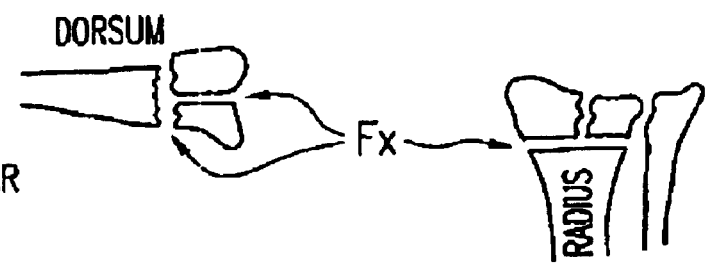
Figure 3:
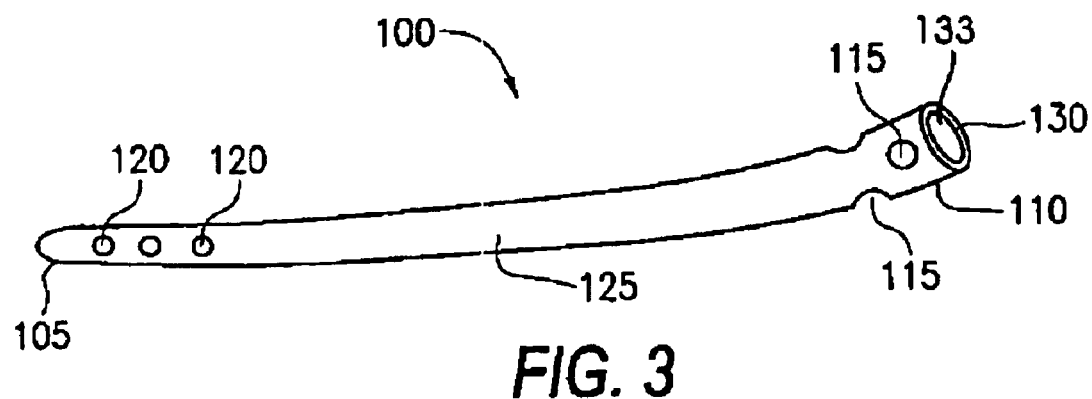
FIG. 3 is a side view of an intramedullary rod.

Referring to FIG. 3, an intramedullary rod 100 includes a diaphyseal end or segment 105, a joint (e.g., the wrist joint) end or segment 110, and mounting sections 115, which may be, for example, implemented as channels 115 that pass through at least a portion of the width of the rod at the joint end 110. The intramedullary rod 100 also may include mounting sections 120, which may be, for example, implemented as channels 120 that are positioned near the diaphyseal end 105 and/or in a mid-region or segment 125 of the rod. The joint end 110 of the rod optionally includes an opening 130 into a longitudinal channel 133 that may extend a short longitudinal distance or may extend the entire length of the rod 100, or any distance in between. As described in detail below, during implantation of the rod 100, the opening 130 receives a guide that is used to ensure that holes drilled through the radius in which the rod is implanted are aligned with the openings 115 and 120 in the rod.

The rod 100 has a generally curved configuration that mimics the curvature of the intramedullary canal of the human radius. The outer diameter and circumferential shape of the rod 100 also varies along its length in a manner that is similar to that of the intramedullary canal. For example, the radius of curvature of the rod may vary along its length between approximately x mm and y mm. The curvature and the variation in outer diameter and circumferential shape also are selected to ensure that the rod 100 fits securely and stably within the intramedullary canal.

For example, the outer diameter of the rod 100 at the joint end 110 may be between approximately 10–25 mm, and more particularly may be between approximately 12–15 mm, and even more particularly may be approximately 14 mm. The outer diameter of the rod 100 at the diaphyseal end may be between approximately 2–9 mm, and more particularly may be approximately between 3–5 mm, and even more particularly may be approximately 3 mm.

Although the rod can have a generally round cross-section, it also can have, for example, an oval cross-section at the joint end 110 and a round or nearly round cross-section at the diaphyseal end 105. This variation in cross-sectional shape along the rod's length is configured to resemble the cross-sectional shape of the intramedullary canal to ensure a secure and stable fit of the rod 100 within the intramedullary canal. Thus, because the inner diameter of the intramedullary canal becomes rounded in the diaphyseal region (i.e., in the direction of the elbow from the wrist joint), the rod is made rounder at its diaphyseal end 105. Similarly, because the inner diameter of the intramedullary canal becomes more oval shaped near the wrist joint, the rod is made more oval at its joint end 110. The cross-sectional shape of the rod 100 along its length and therefore may be fabricated to gradually transition from an oval to a round shape, although a completely round cross-sectional shape along its entire length also will function adequately.

Figure 4:
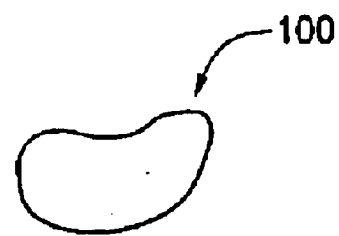
FIG. 4 is a cross-sectional side view of one implementation of the intramedullary rod.

Referring to FIG. 4, the cross-sectional shape of the rod 100 also can be lima-beaned shaped to closely configure to the cross-sectional shape of the intramedullary canal. However, for ease of manufacturing, a generally round or oval shape can be used.

Figure 5:
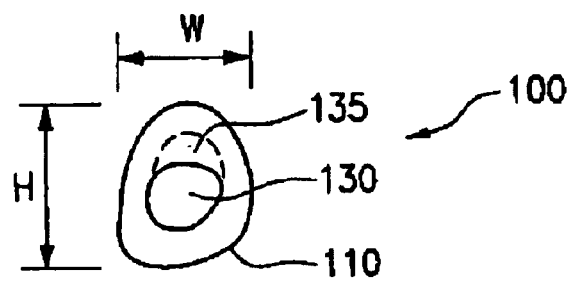
FIG. 5 is an end view of the intramedullary rod of FIG. 3.

Referring to FIG. 5, in one implementation the joint end 110 of the intramedullary rod may be configured with an oval shape having a height H of approximately 15 mm or less and a width of approximately 5 mm or less. The opening 130 at the joint end, however, is generally round so that it can accept a guide having a threaded mounting piece. If the guide has a non-threaded mounting piece such as, for example, a friction fit mounting piece, the opening can be of any shape, such as, for example, an oval shape 135 or a key shape configured to mate with a keyed mounting piece of the guide.

The length of the rod 100 is between approximately 50 mm and 100 mm, and may be fabricated, for example, in lengths of approximately 50 mm, approximately 80 mm, and approximately 100 mm. Of course, the rod can be fabricated in any length desirable. By comparison, the length of an average human radius is approximately 170 mm. Thus, the rod 100 is inserted into the typical intramedullary canal a distance that is less than half the length of the canal. Although the rod 100 can be fabricated to various lengths, the inventor anticipates that a single rod of an optimum length can be used in the majority of all of the cases in which a rod will be used for treatment of a radius fracture. Moreover, because the radius of curvature of the rod generally matches the radius of curvature of the typical intramedullary canal, surgeons will be able to use a standard size rod in the majority of all cases, as well as in both the right radius in the left radius.

The rod 100 is made of a rigid, biocompatible metal, plastic, or ceramic. The metals can be but are not limited to, for example, titanium, titanium alloys, stainless steel alloys, cobalt-chromium alloys, and biocompatible castable metals. The plastic materials can be but are not limited to, for example, resorbable plastics, such as lactosorb, beta lactans, polyglycolic acid, and polylactic acid.

The mounting sections or channels 115 and 120 may be, for example, threaded or smooth walled, depending upon the type of pin, screw, tensioning device, or tine that will be used to fix the rod 100 in the intramedullary canal and to the bone fragment or fragments. Typically, a pin, a screw, or a tensioning device will be used to fix the rod 100 in the intramedullary canal and a tensioning device or a tine will be used to fix the rod to the bone fragment or fragments. Because the diaphyseal region of the bone is generally hard, bone screws can be used to secure the rod to the bone. However, because the bone in the epiphyseal and metaphyseal regions are generally not as hard, bone screws are less likely to be used to secure the rod to the bone or bone fragments.

Figure 6:
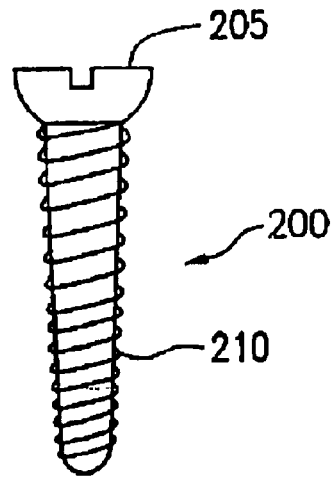
FIGS. 6 and 7 are side views of bicortical bone screws for use with the intramedullary rod of FIG. 3.

For example, referring to FIG. 6, the tensioning device used to fix the rod within the intramedullary canal may be a threaded pin or screw 200 that includes a head 205 and a threaded shank 210. In use, the screw 200 is passed through one side of the radius, one channel 120, and into the other side of the radius. The head 205 is seated in a pocket in the first side of the radius.

Figure 7:
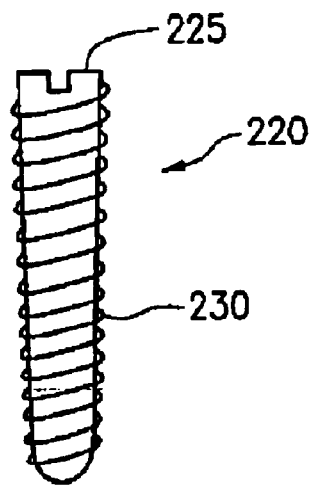

Referring to FIG. 7, a threaded pin or screw 220 includes a low profile head 225 and a threaded shank 230. The screw 220 is implanted in a radius through the intramedullary rod 100 in the same manner as the screw 200. The head 225, however, can be inserted to be flush with the outer surface of the radius. The screws 200 and 220 are threaded along their entire shank and, as such, are threadably attached to both cortexes of the radius. Thus, these screws are typically referred to as bicortical screws. They advantageously provide two points of threaded fixation to the radius in which they are implanted. If the pitch of the threads are spaced apart enough, they can loosely mate with threads in the channel 120 to further stabilize the position of the rod in the intramedullary canal. The threads also can be configured to tightly mate with the threads in the channel 120 to provide better stabilization of the rod in the intramedullary canal.

Figure 8:
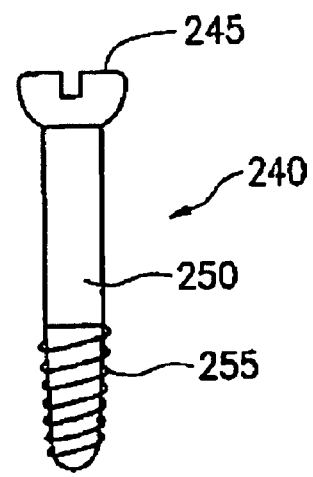
FIGS. 8 and 9 are side views of unicortical bone screws for use with the intramedullary rod of FIG. 3.

Referring to FIG. 8, a unicortical screw 240 includes a head 245, a threadless shaft portion 250, and a threaded shaft portion 255. Like the screw 205, when the screw 240 is implanted, the head 245 is seated in a pocket in a first side or cortex of the radius and the threaded shaft portion 255 is threaded into the second side or cortex of the radius. The threadless shaft portion 250 passes through the channels 120 and fixes the position of the rod in the intramedullary canal.

Figure 9:
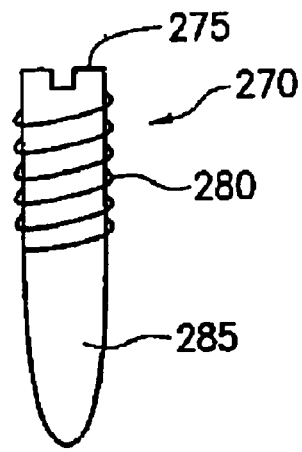

Referring to FIG. 9, a unicortical screw 270 includes a head 275, a threaded shaft portion 280, and a threadless shaft portion 285. The head 270 is configured to be flush with the side or cortex of the radius in which the threaded shaft portion 280 is threaded. The threadless shaft portion 285 passes through the channels 120 and fixes the position of the rod in the intramedullary canal.

Figure 10:
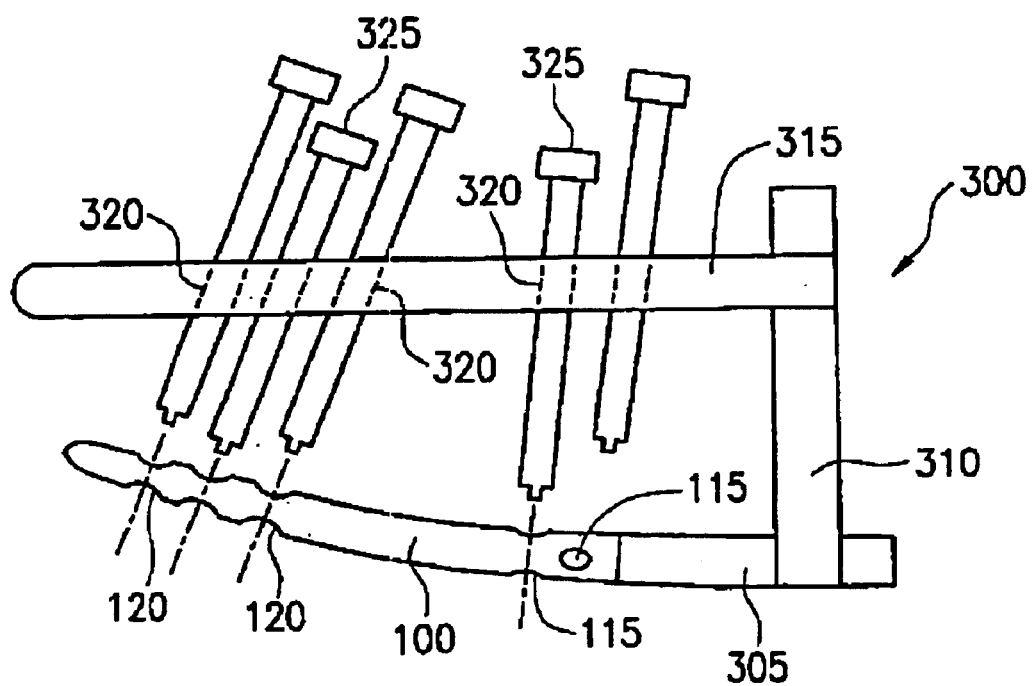
FIG. 10 is a side view of a guide mounted to the intramedullary rod of FIG. 3.

Referring to FIG. 10, a guide 300 is used during implantation of the rod 100 to line up drill holes through the radius with the mounting sections or channels 115 and 120 in the rod. The guide 300 includes a mounting piece 305, a handle 310, and an aiming piece 315. The mounting piece 305 mounts to the joint end 110 of the rod 100. For example, the opening 130 at the proximal end can be shaped or keyed and the mounting piece 305 can have a shaped end or a keyed end that mates with the shape or key of the opening 130 so that the mounting piece can be inserted into the guide in only one position. The arrangement of the handle 310 and the aiming piece 315 relative to the mounting piece is fixed so that channels 320 passed through the aiming piece and are aligned with the mounting sections or channels 115 and 120 in the rod 100. Drill guides 325 are positioned in the channels 320 to guide drill bits (not shown).

Although FIG. 10 shows five dull guides 325 positioned within the aiming piece 315, the guide 300 may be accompanied by a single drill guide 325 that can be removed and reinserted in another channel 320. FIG. 10 also shows the proximal-most channel 115 being positioned at a 90° rotation from the other mounting sections or channels 115, 120. The guide 300 is configured such that the handle 310 can be moved relative to the mounting piece 305 in 90° increments so that the channels 320, drill guides 325, and the channels 115 and 120 are aligned.

To implant the intramedullary rod 100, the surgeon exposes the area around the fracture using standard surgical techniques. The surgeon next drills a hole from the dorsal or lateral end of the distal fragment of the radius into the intramedullary canal through which the rod can be inserted. The rod 100 with the guide 300 mounted to it then is inserted through the hole into the intramedullary canal of the fragment and of the radius. The surgeon then rotates the guide 300 until the rod 100 is properly oriented within the canal. The surgeon then drills holes through the dorsal radius, fragment, and channels 115. Depending upon the tine, tined device, or tensioning device used to secure the fragment, openings of various sizes in the dorsal radius may be made through which the tine, tined device, or tensioning device is inserted. The surgeon then inserts a drill bit into one of the drill guides and drills a hole through the first cortex. After the first cortex is drilled, the surgeon advances the drill bit through the channel 120 in the rod 100 and up against the second cortex, at which point the surgeon drills a hole through the second cortex. A bone screw then is screwed through the first cortex into the rod. A second and/or additional holes may be drilled and a second and/or additional bone screws may be placed, if necessary or desired, through the diaphyseal segment of the rod and radius to secure the rod within the intramedullary canal. Although FIG. 10 shows an intramedullary rod with three openings 120 passing through the intramedullary rod, the rod can have more or fewer openings 120.

The bone screws fix the position of the intramedullary rod within the intramedullary canal of the radius. However, the bone screws do not fix the position of the distal radius fragment with respect to the radius or the intramedullary rod. Instead, tines, tine-like devices, or tensioning devices are used to fix the position of the distal fragment or fragments relative to each other, the intramedullary rod, and the radius. The tines can be of any configuration that is mountable to the intramedullary rod and is rigid enough to pass through the fragment or fragments and fix the position of the fragments. For example, the tines can be threadably mounted, snap fit mounted, press fit mounted, or keyed to the intramedullary rod. The tines generally are placed within the intramedullary rod and canal after the intramedullary rod is positioned within the intramedullary canal, and pass through the intramedullary rod in an orientation that is generally perpendicular to the longitudinal axis of the intramedullary canal.

Figure 11:
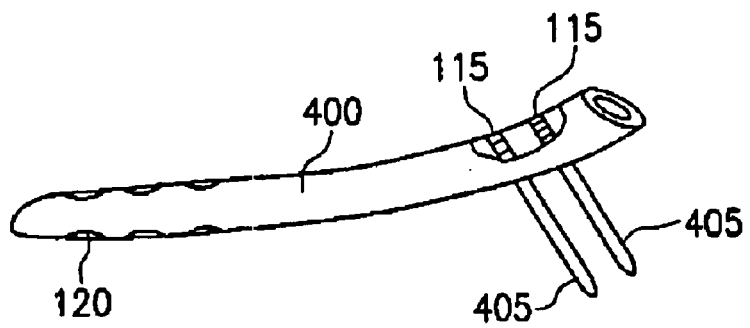
FIG. 11 is a side view of an intramedullary rod configured to receive individual tines.
Figure 12:
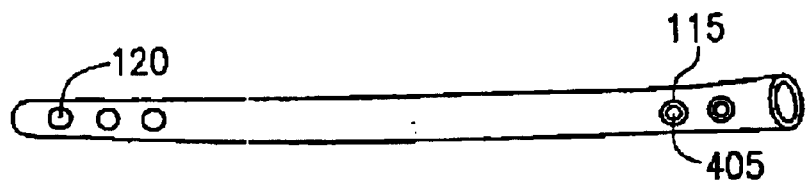
FIG. 12 is a top view of the intramedullary rod of FIG. 11.

For example, referring to FIGS. 11 and 12, the intramedullary rod 400 may be configured to use individual tines 405 that have a shaft and are passed through the intramedullary rod into the bone fragments and mounted to the rod. The tines 405 may be, for example, threadably mounted to the rod, although other mounting and fastening means may be used. The tines 405 are configured to be in a parallel arrangement relative to each other and may be in the same plane as, or a perpendicular plane to, the bone screws that pass through the openings 120.

Figure 13:
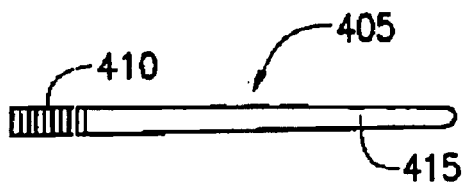
FIG. 13 is a side view of a tine having a threaded head.

Referring to FIG. 13, the tines 405 include a first threaded section 410 and a second non-threaded section 415. The channels 115 through which the tines 405 pass are threaded and the tines 405 are threadably received in the channel 115. The first threaded section 410 has a length that is approximately the same as the length of the threaded channel 115. The head of the tine 405 can be configured to receive an Allen wrench, a conventional screwdriver, a Phillips head screwdriver, or another inserting tool that can be used to threadably insert the tine.

Figure 14:
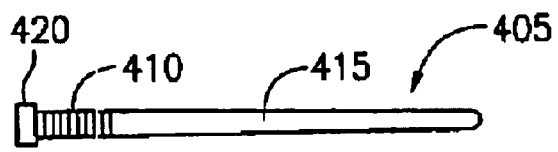
FIG. 14 is a side view of a tine having a head and a threaded shaft portion.

Referring to FIG. 14, a second embodiment of the tine 405 includes a head 420 and the channel 115 includes a countersunk opening configured to receive the head. The head 420 can be configured to receive any of the insertion tools described above. The head also can be configured in a variety of shapes, such as an angled base, a flat base, and a rounded or tapered base, and the countersunk opening can be reciprocally configured to receive the head.

Figure 15:
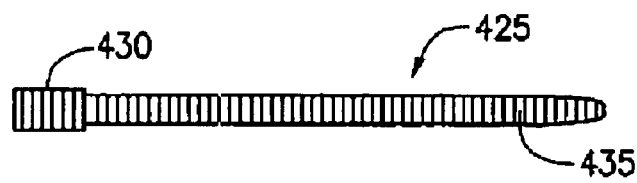
FIG. 15 is a side view of a tine having a threaded head and a threaded shaft.

Referring to FIG. 15, a threaded tine 425 includes a threaded head 430 configured to be threadably received in the threaded channel 115 and a threaded shank 435 configured to be threadably received in the bone fragments, and may be threadably mated to the bone fragments. The threaded shank 435 maintains the position of the bone fragments relative to the radius and secures the intramedullary rod to the bone fragments. The pitch and depth of the threads of the threaded section 435 can be greater and deeper, respectively, than the pitch and depth of the threads of the threaded head 430. In this manner, the threads along the threaded shank will securely grab the bone fragments to prevent their inadvertent movement.

Figure 16:
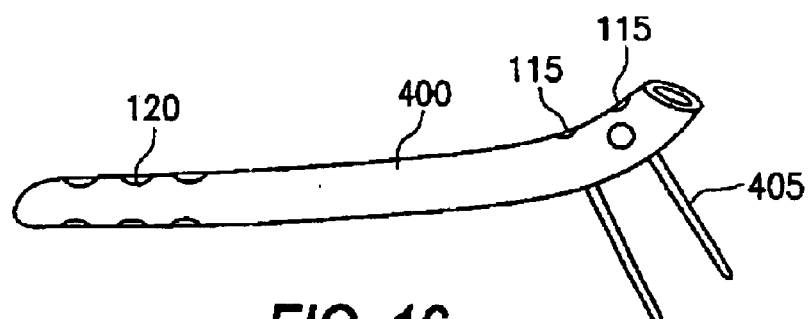
FIG. 16 is a side view of the intramedullary rod of FIG. 11 being configured to receive a bone screw for fixation at a perpendicular angle to the tines.
Figure 17:
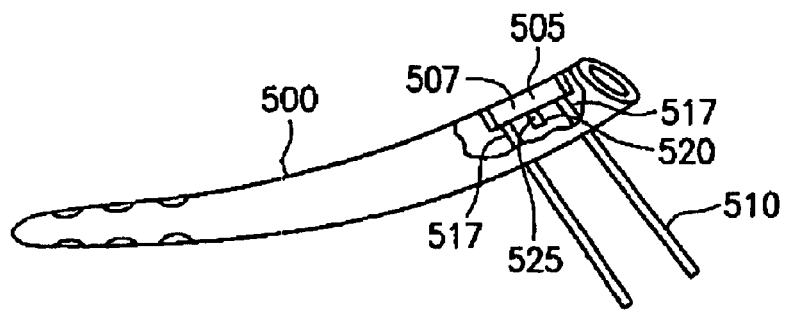
FIG. 17 is a side view of an intramedullary rod configured to receive a tined insert.
Figure 18:
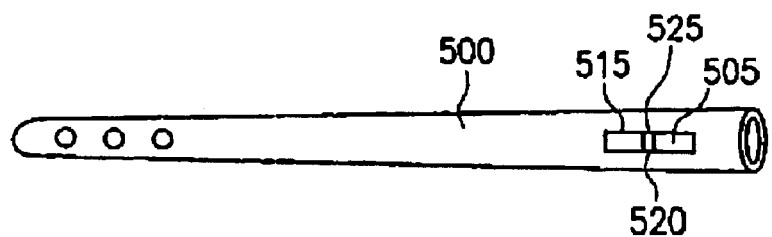
FIG. 18 is a top view of the intramedullary rod of FIG. 17.
Figure 19:
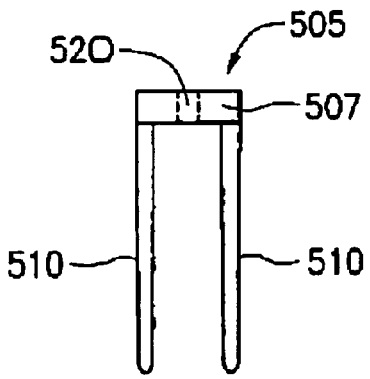
FIGS. 19–21 are a side view, top view, and bottom view, respectively, of the tined insert of FIG. 17.
Figure 20:
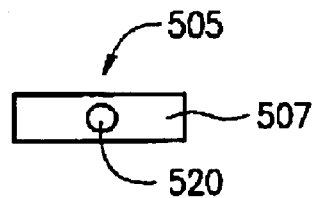
Figure 21:
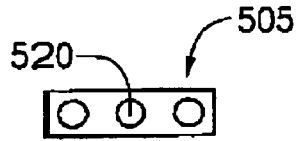
Figure 22:
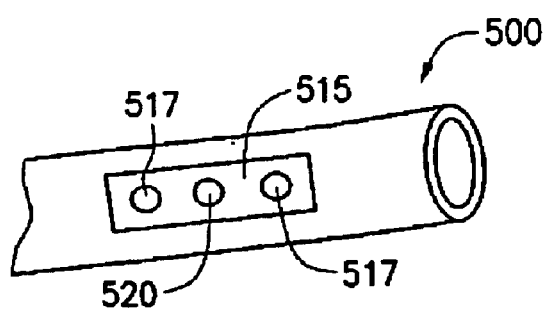
FIG. 22 is a top view showing an opening in the intramedullary rod for receiving the tined insert.

Referring to FIG. 16, the tines 405 can be spaced apart such that a bone screw or tensioning device can be passed through the intramedullary rod 400 from a different orientation than the tines to further secure the rod to the bone fragments. This provides additional fixation of the rod to the bone fragments. By securing the rod to the bone fragments from a different orientation, undesirable rotation and movement of the bone fragments is further restricted. Of course, the bone screw or tensioning device can be configured as the threaded tine 425.

Referring to FIGS. 17 through 22, an intramedullary rod 500 can be configured to receive a tined insert 505 that includes a rectangular block 507 from which a pair of integrally formed or integrally mounted tines or shafts 510 extend. The tined insert 505 also can be formed with a single tine 510. The intramedullary rod 500 includes an opening 515 that is configured to receive the tined insert 505 and a pair of openings 517 that pass through the rod and are configured to receive the tines 510 when the tined insert is positioned within the opening 515. The intramedullary rod 500 also includes a threaded opening 520 that extends from the opening 515 into the rod and that is configured to receive a mounting screw 525 to mount the insert 505 to the intramedullary rod 500. When the surgeon is drilling through the dorsal radius, he must provide an enlarged opening through which the tined insert fits.

The tined insert 505 is made from a rigid and strong, biocompatible material, such as a stainless steel or titanium alloy, or a plastic, and the tines are formed integrally with or are mounted to the block 507. The block can be rectangularly shaped, or of any other shape, and the opening 515 can be reciprocally shaped to receive the block. The tines can be press fit into openings in the block, threadably mounted to the block, welded to the block, adhered to the block, injection molded with the block, or formed with the block by removing material from between the tines to form the tines.

Figure 23:
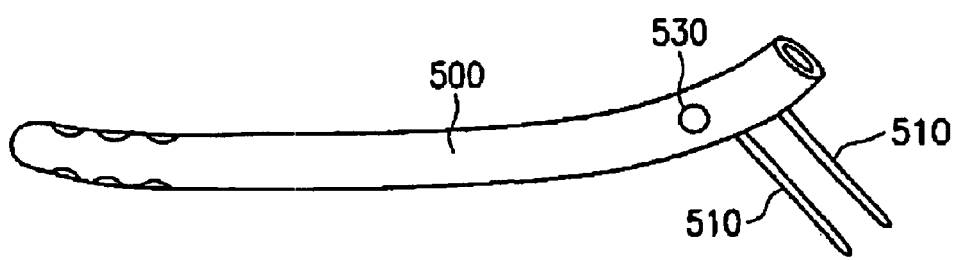
FIG. 23 is a side view of the intramedullary rod of FIG. 17 being configured to receive a bone screw for fixation at a perpendicular angle to the tines.

Referring to FIG. 23, the tines 510 can be spaced apart such that a bone screw or a tensioning device can be passed through the intramedullary rod 500 from a different orientation than the tines to secure the rod to the bone fragments. This provides additional fixation of the rod to the bone fragments. By securing the rod to the bone fragments from a different orientation from the tines, undesirable rotation and movement of the bone fragments is further restricted.

The intramedullary rod 500 is implanted as described above and the tines then are inserted through the openings 515 and 517 into the bone fragment or fragments. The screw 525 then is threadably inserted through the block 507 into the opening 520 to mount the tined insert 505 to the rod 500. A bone screw or tensioning device then may be passed through the opening 530 to provide more fixation of the bone fragment or fragments to the rod.

Figure 24:
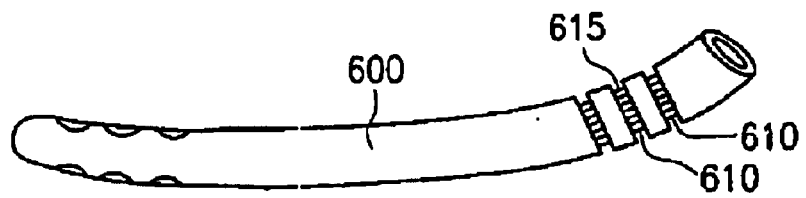
FIG. 24 is a side view of an intramedullary rod configured to receive snap fit tines.
Figure 25:
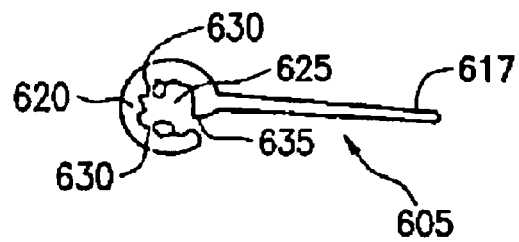
FIGS. 25 and 26 are front and side views of the snap fit tines for mounting to the intramedullary rod of FIG. 24.
Figure 26:
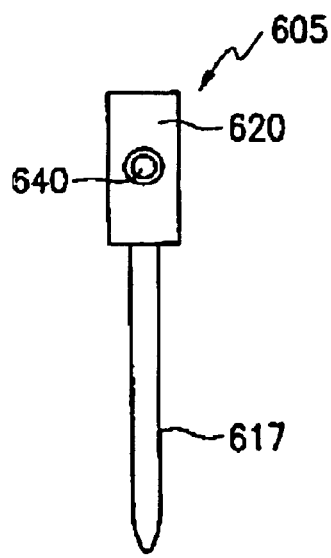

Referring to FIGS. 24–26, an intramedullary rod 600 can be configured to receive snap fit tines 605. The rod 600 includes mounting sections or circumferential channels 610, having teeth or recesses 615, into which the snap fit tines 605 are placed. The snap fit tine 605 includes tines 617 and a head 620 having an opening 625 into which teeth 630 protrude. The head 620 also includes a slot 635 that interrupts the continuity of the circumference of the head. In this manner, the slot 635 can be enlarged to permit the head to slide over the rod 600. The edges of the head which define the slot can be angled to allow easier opening of the slot by engagement of the slot with the mounting sections 610. The teeth 630 are configured to fit within or mate with the teeth or recesses 615 to form a secure engagement or fit that resists rotational movement of the snap fit tines 605 relative to the intramedullary rod 600. The head 620 also includes at least one threaded opening 640 into which a threaded screw or bolt can be threadably inserted to form an interference fit against the mounting sections 610. In this manner, the position of the snap fit tine 605 can be better fixed relative to the rod 600.

The snap fit tine 605 is mounted to the rod 600 by enlarging the slot 635 by pushing the snap fit tine 605 against and over the mounting section 610, orienting the tine 617 into the opening through the bone fragment, and releasing the head to allow the slot 635 to close to its original distance. A screw then is inserted into each opening or openings 640 and tightened against the mounting section 610 to fix the position of the tine relative to the rod.

Figure 27:
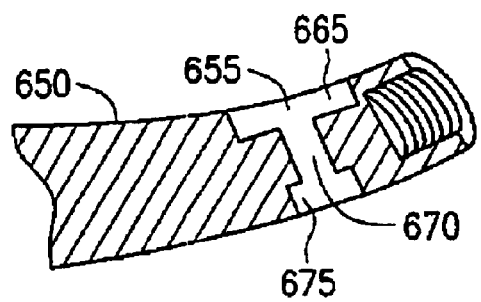
FIG. 27 is a cross-sectional side view of an intramedullary rod configured to receive a press fit tine.
Figure 28:
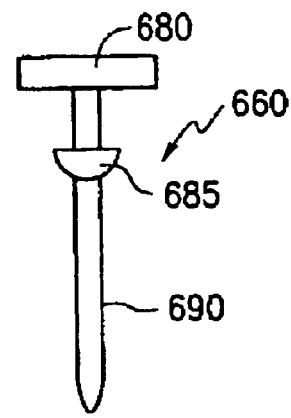
FIG. 28 is a side view of the press fit tine of FIG. 27.
Figure 29:
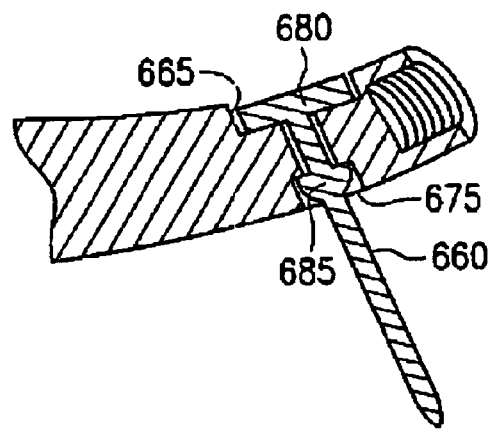
FIG. 29 is a cross-sectional side view of the intramedullary rod of FIG. 27 with the press fit tine inserted.

Referring to FIGS. 27–29, an intramedullary rod 650 includes an opening 655 that is configured to receive a press fit tine 660. The opening 655 includes a first, wide portion 665, a second, narrow portion 670, and a third, wide portion 675, with the second portion positioned between the first and third portions. The tine 660 includes a head 680 and a stop 685 that extends from a shaft 690. The position of the head 680 relative to the stop 685 is approximately the same as the position of the first portion 665 relative to the third portion 675. The size of the first portion 665 also is approximately the same as the size and the head 680 and the size of the third portion 675 is similar to the size of the stop 685. In this manner, the tine 660 can be inserted into the opening 655 by passing the shaft 690 through the first portion 665, the second portion 670, and the third portion 675 until the head 680 rest within the first portion 665. By inserting the tines in this fashion, the stop 685 is pressed through the second, narrow portion 670 until it is in the third portion 675, at which point the diameter of the stop will prevent it from being pulled out in the reverse direction from which it was inserted.

Figure 30:
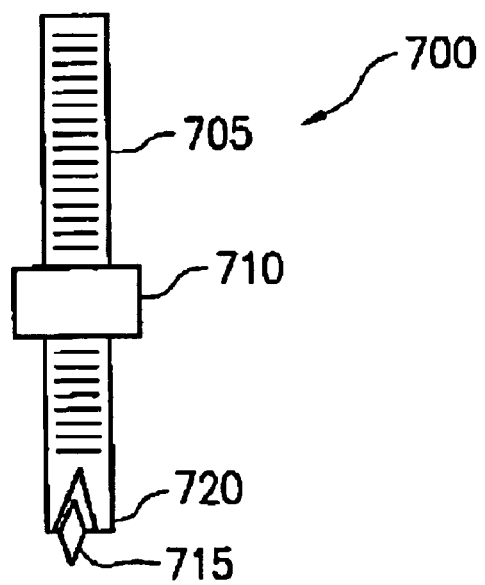
FIG. 30 is a front view of a tie band fastener for securing an intramedullary rod.

After the intramedullary rod is positioned within the intramedullary canal, the bone screws are passed through the bone into the intramedullary rod, and the tines are fixed within the rod and the bone fragments, the surgical site is closed. To reduce the amount time that the procedure takes, substitutes for, or variations of, the bone screws can be used. These substitutes and variations can be bone screws, connectors, or other tensioning devices. For example, the connectors can be in the form of any device that functions to fix the intramedullary rod to the radius. For example, referring to FIGS. 30 and 31, a tensioning device can be implemented as a tie band fastener 700 that includes a tie band 705, a slidable tab 710, and a stop 715. The slidable tab 710 is configured to slide in one direction along the tie band 705 using techniques that are well-known in the art. The stop 715 is positioned at the end of the tie band 705 and may be pivotally attached to a bar 720 such that the stop can be aligned with or perpendicular to the tie band. In general, the stop 715 is mounted to the tie band such that it has a narrow width when being passed through the rod and radius and has a wider width after it exits the radius, such that it prevents the tie band from being pulled back through the radius.

Figure 31:
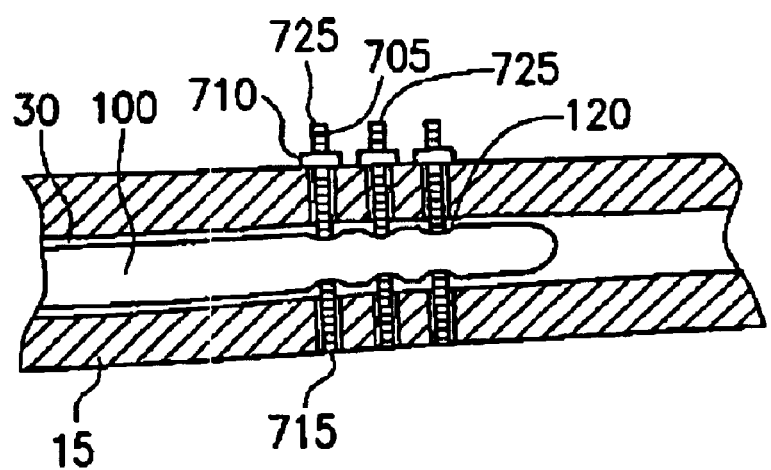
FIG. 31 is a partial cross-sectional side view of the tie band fastener of FIG. 30 being used to secure an intramedullary rod within the diaphyseal region of the radius.

As illustrated in FIG. 31, to use the tie band fastener 700, the stop 715 and adjacent end of the tie band 705 are inserted through one of the openings 120 in the intramedullary rod 100 and into a pre-drilled hole through the radius 15 and the intramedullary canal 33. Once the stop passes through the hole, the physician pulls back the tie band so that the stop 715 will pivot into a position that is generally perpendicular to the tie band and pressed against the bone. In this configuration, the tie band fastener 700 cannot be pulled back out of the hole. The slidable tab 710 then is pushed down along the tie band 705 until it is positioned firmly against the side of the radius that is opposite from where the stop is positioned. A portion 725 of the tie band that extends beyond the slidable tab 710 then may be cut and discarded.

Figure 32:
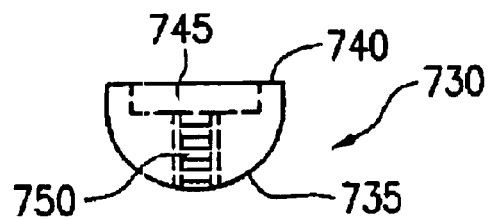
FIG. 32 is a side view of a fastener for use with the tie band of FIG. 30.
Figure 33:
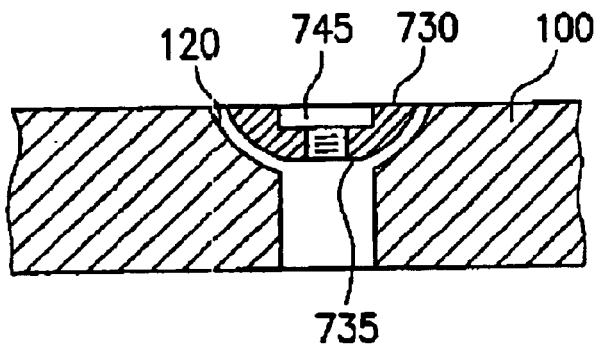
FIG. 33 is a cross-sectional side view of the fastener of FIG. 32 positioned within an opening.
Figure 34:
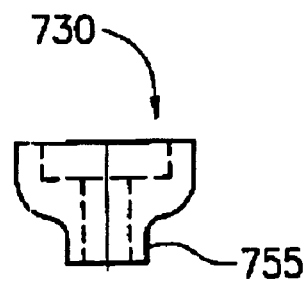
FIG. 34 is a side view of the fastener of FIG. 32 with an extended base.

A number of variations of the tie band described above can be used as a tensioning device to hold the device to a bone. For example, referring to FIGS. 32 and 33, a fastener 730 can be configured with a rounded base 735 to angulate within the openings in the cortex of the intramedullary canal and a flat top 740 to be generally flush with the outer surface of the radius. By allowing angulation within the openings in the cortex, there is more flexibility for varying the orientation of the tie band through the radius in the intramedullary rod. The fastener 730 also can have a recess 745 in the top 740 so that the tie band 705 can be cut to leave the remaining end within the recess. In this manner, the remaining end will not be in contact with tissue, which can be irritable to the tissue and/or painful if there is substantial movement of the tissue against the remaining end. The fastener 730 also includes a channel 750 passing between the base 735 and the top 740 and which is ribbed to allow movement of the tie band in one direction. Referring to FIG. 34, the fastener 730 can be configured to have an extension 755 protruding from the rounded base 735. The extension provides extra land for retaining the tie band, which provides a more secure placement of the tie band in the fastener 700.

Figure 35:
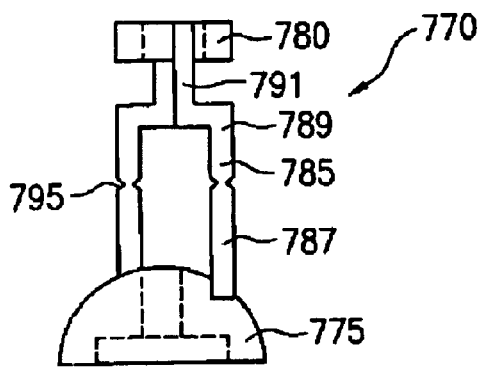
FIGS. 35 and 36 are front and side views, respectively, of a Molly bolt system used as a tensioning device to secure an intramedullary rod within an intramedullary canal.
Figure 36:
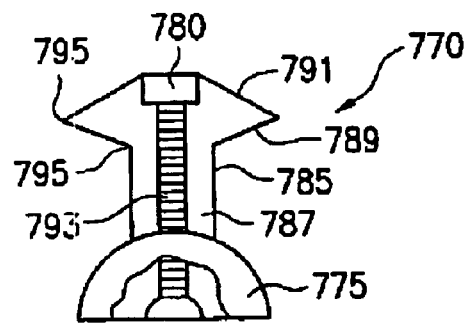
Figure 37:
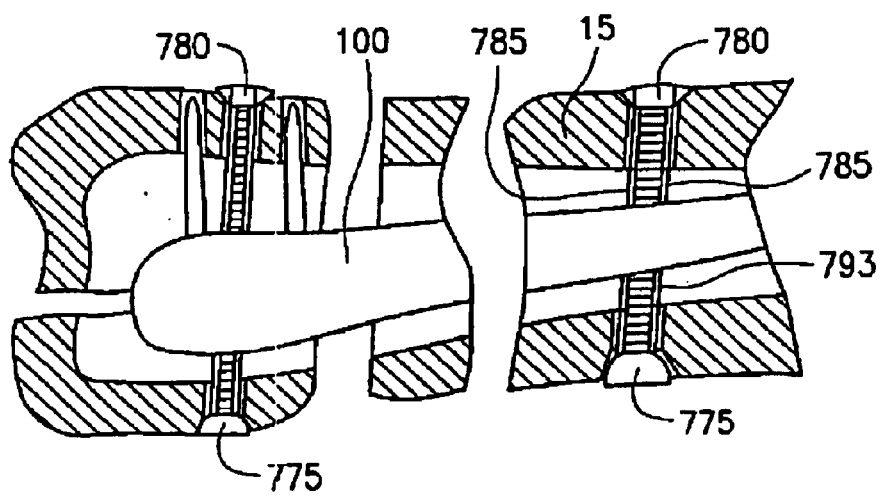
FIG. 37 is a partial cross-sectional side view of an intramedullary rod secured within a radius using the Molly bolt system of FIGS. 35 and 36.

Referring to FIGS. 35–37, a molly bolt system 770 also can be used as a tensioning device to hold the intramedullary rod 100 to the radius 15. The molly bolt system 770 includes a head 775, a nut 780, and one or more flexible arms 785 extending between the head and the nut. Each arm 785 includes a first length portion 787, a second length portion 789, and a third length portion 791. The nut 780 is threaded such that when a physician inserts a screw 793 through the head 775 into the nut 780, tightening the screw will pull the nut towards the head. The arms 785 can be formed one or more with weakening notches 795 strategically placed by the physician or the manufacturer at predetermined positions such that the arms will have a tendency to bend or fold at those positions during tightening of the screw. The second length portion 789 and the third length portion 791 may be offset from each other so that when they are folded together, they form a flat surface with a low profile.

The notches 795 can be placed such that the first length portion 787 is within the radius and the second length portion 789 and the third length portion 791 are configured to fold up against or adjacent to each other when the nut 780 is tightened and pulled towards the head. By estimating the diameter of the radius from a radiograph, the physician can form notches 795 at a position on the first length portion 787 that corresponds to the edge of the channel in the bone from which the nut 780 will protrude. The second length portion 789 and the third length portion 791 also can be notched to fold over, or fold to a position adjacent to, each other and thereby form an obstacle to completely pulling the nut 780 into the channel, although the nut may be somewhat recessed within the channel. Moreover, as illustrated in FIG. 37, the molly bolt system 770 advantageously can be used to set the position of the bone fragment or fragments relative to each other by the degree to which the nut 780 is tightened towards the head 775.

Alternatively, the molly bolt system 770 can be configured so that the second length portion 789 and the third length portion 791 are configured to overlap against each other when folded together to provide a more rigid member that resists pulling into the channel through the bone under extreme tension loads.

Figure 38:
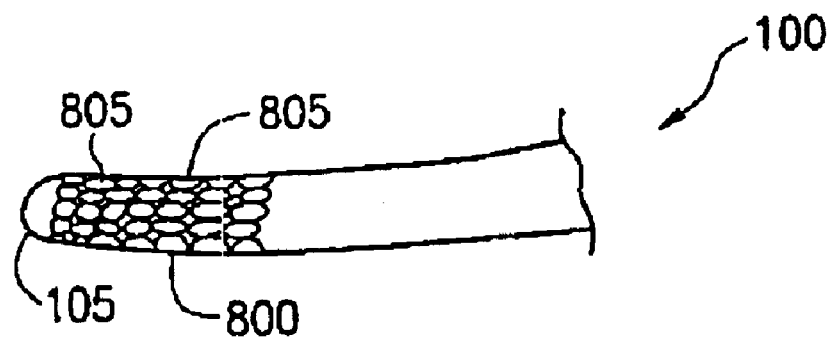
FIG. 38 is a side view of an intramedullary rod having a diaphyseal section with a dimpled surface.
Figure 39:
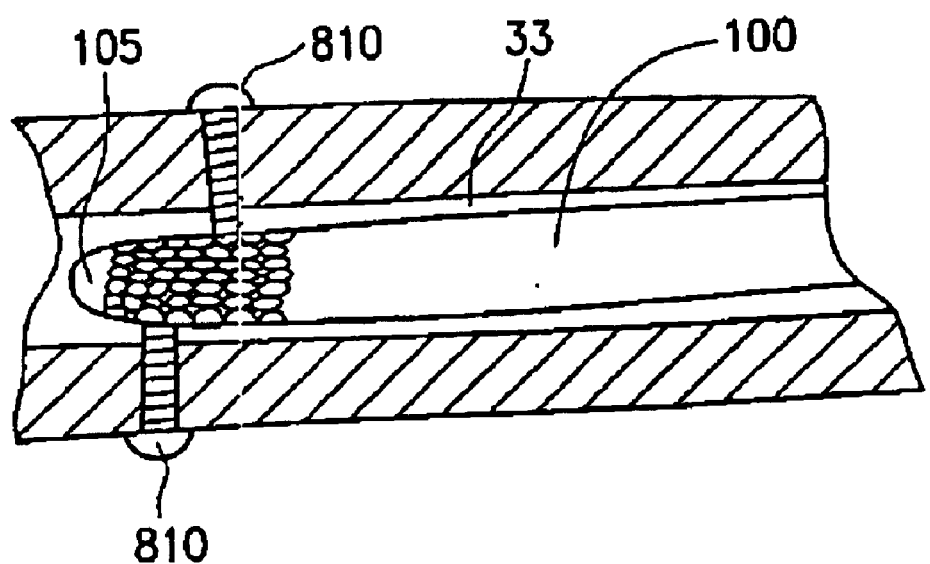
FIG. 39 is a partial cross-sectional side view showing the intramedullary rod of FIG. 38 secured within an intramedullary canal using bone screws.

Referring to FIGS. 38 and 39, the intramedullary rod 100 can be configured to include a dimpled surface 800 at the diaphyseal end 105. The dimpled surface 800 can be configured to include individual dimples 805 that are deep enough to seat the end of a screw 810. In this manner, the screw 810 can be inserted through the radius until it seats against a dimple 805. Using a second screw 810, and optional additional screws 810, the diaphyseal end 105 can be fixed in position within the intramedullary canal 33. This method of fixing the diaphyseal end 105 advantageously allows the physician to place screws 810 with less concern for alignment of the screws with a channel through the intramedullary rod because the screws will seat against the rod, even when inserted from almost any orientation.

Figure 40:
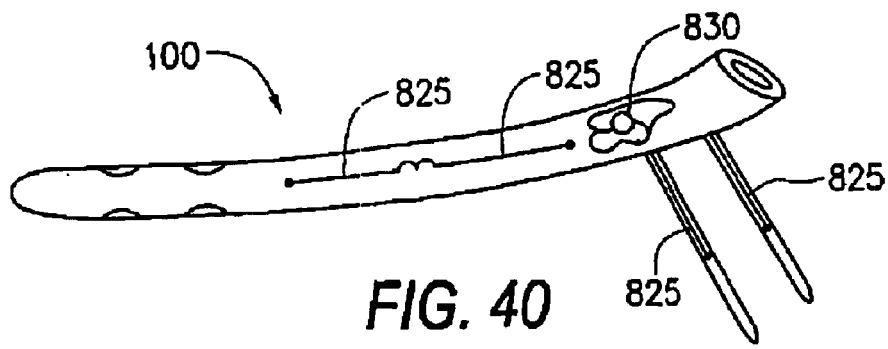
FIG. 40 is a side view of an intramedullary rod having tensiometers mounted along its length and on its tines to measure strain.
Figure 41:
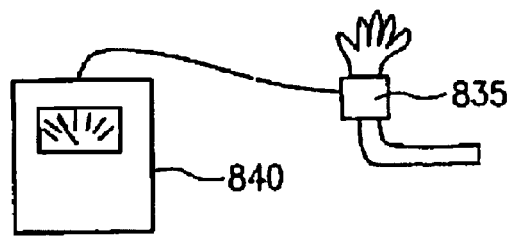
FIG. 41 is a plan view of a system for monitoring the tension in the intramedullary rod of FIG. 40.

Referring to FIGS. 40 and 41, the intramedullary rod 100 can be modified to include one or more tensiometers 825 mounted to the tines and along the length of the rod, and electrically connected to a transmitter 830 that is mounted to the rod 100, is positioned within the rod, or is left in a subcutaneous pocket in the patient's arm. The tensiometers 825 can be implemented as strain gauges that provide a measure of the amount of strain on one or more of the tines and along the length of the rod. The physician can monitor the trend of strain over time until the strain value appears to be unchanging, which is indicative of adequate healing. To measure the strain, a monitor 835 can be placed over the transmitter 830 and used to remotely turn on and off the transmitter and to monitor the strain values using a display 840.

Figure 42:
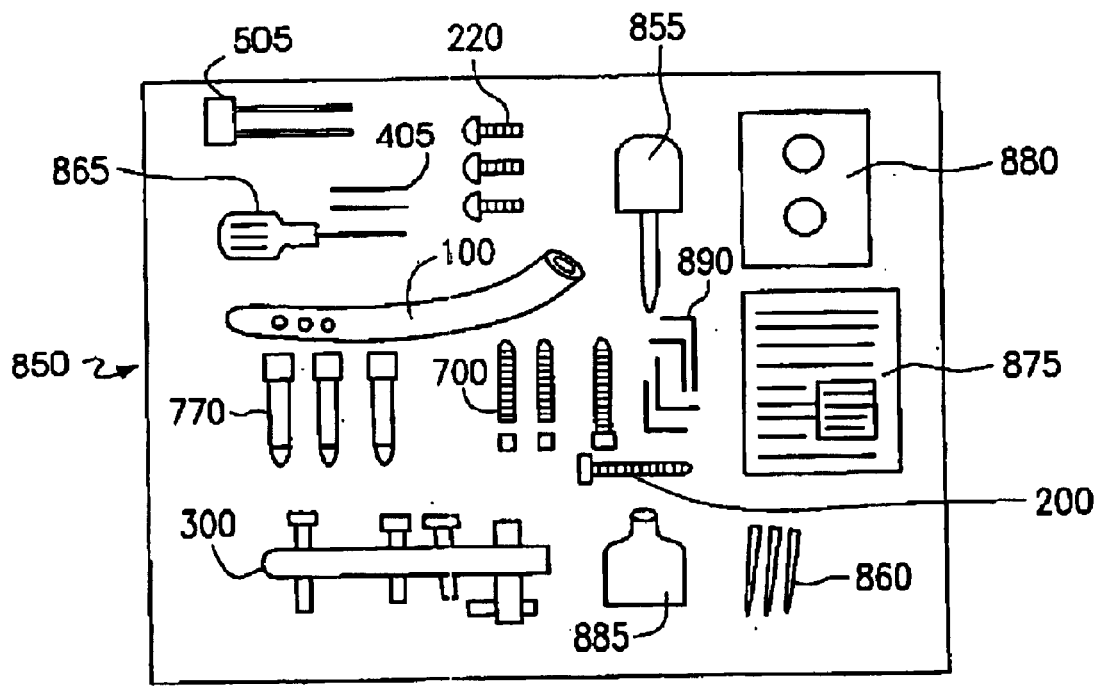
FIG. 42 is a plan view of an intramedullary rod kit.

Referring to FIG. 42, the intramedullary rod kit 850 is configured to include the intramedullary rod 100 and other tools necessary to perform the implantation, as well as any of the devices and accessories described herein. For example, the kit 850 can include a drill 855; drill bits 860 covering a range of sizes; the guide 300; tensioning devices, such as the bone screws 200, 220, 240, and/or 270, the molly bolt system 770, the tie bands 700; a screw driver 865 or a set of allen wrenches 870 to place the bone screws; one or more of the tined inserts 505, the individual tines 405, the threaded tines 425, the snap fit tines 605, and/or the press fit in tine 660; instructions for use 875; an instructional video 880; and/or therapeutic agents 885 to apply to the device or to the injury site. The therapeutic agents can include a bone growth regulating protein and/or a platelet derived growth factor. Providing these items in a kit form is advantageous to the physician because there is no need to search for or attain overlooked items that may be necessary for the procedure because all of the items are included. Providing an instructional video with the kit or separately is advantageous to the physician because the physician can view the video as often as necessary until the required degree of comfort and confidence in performing the procedure is attained to actually undertake the procedure. By providing the items necessary to perform the procedure and the instructional video and instructions for use together provide advantages to physicians because the required learning and understanding can be quickly attained while manipulating and examining the necessary articles needed for the procedure.

A number of embodiments of the intramedullary rod and accessory devices and components have been described. Nevertheless, it will be understood that various modifications may be made without departing from the spirit and scope of the invention. For example, the rod, tines, and/or tensioning devices can be coated with a therapeutic agent by the manufacturer or by the physician at implantation to treat any condition to which the bone in which they are implanted within may be subject to. Moreover, the rod, tines, and tensioning devices may be configured for implantation in any intramedullary canal, including but not limited to, the bones of the leg, arm, toe, finger, hip, and/or shoulder regions. For example, the diameter, the shape, and/or the radius of curvature of the rod may be modified to allow secure implantation of the rod in any of these regions and bones by designing the rod to resemble the intramedullary canal of the selected region of implantation. Accordingly, other embodiments are within the scope of the following claims.

What is claimed is:

1. An intramedullary rod kit for fixation of a distal radius fracture, the intramedullary rod kit comprising:
   an intramedullary rod comprising:
      a diaphyseal segment including at least one first mounting section configured to receive a tensioning device,
      a middle segment; and
      a joint segment including at least one second mounting section configured to receive a tine,
   wherein the diaphyseal segment, the middle segment, and the joint segment define a curved configuration that is substantially similar to a curvature of the intramedullary canal of a human radius; and
   at least one tine, wherein the tine comprises an insert from which at least one shaft extends and wherein the insert is configured to be mated to the second mounting section.

2. The intramedullary rod kit of claim 1, wherein an outer diameter of the intramedullary rod varies between approximately 10 mm and 25 mm at the joint segment and approximately 2 mm and 9 mm at the diaphyseal segment.

3. The intramedullary rod kit of claim 1, wherein an outer diameter of the intramedullary rod varies between approximately 12 mm and 15 mm at the joint segment and approximately 3 mm and 5 mm at the diaphyseal segment.

4. The intramedullary rod kit of claim 1, wherein an outer diameter of the intramedullary rod varies between approximately 14 mm at the joint segment and approximately 3 mm at the diaphyseal segment.

5. The intramedullary rod kit of claim 1, wherein the joint segment has a round cross-section or an oval cross-section.

6. The intramedullary rod kit of claim 1, wherein the diaphyseal segment has a round or a generally round cross-section.

7. The intramedullary rod kit of claim 1, wherein a length of the rod is between approximately 50 mm and 100 mm.

8. The intramedullary rod kit of claim 1, wherein a length of the rod is approximately 80 mm.

9. The intramedullary rod kit of claim 1, further comprising written instructions for use.

10. The intramedullary rod kit of claim 1, further comprising an instructional video.

11. The intramedullary rod kit of claim 1, further comprising a drill bit configured to drill a hole in bone tissue.

12. The intramedullary rod kit of claim 1, wherein the diaphyseal segment of the intramedullary rod comprises a dimpled surface.

13. The intramedullary rod kit of claim 1, wherein the intramedullary rod, and/or the tine are coated with a therapeutic agent.

14. The intramedullary rod kit of claim 1, wherein the shaft is integrally formed with the insert.

15. The intramedullary rod kit of claim 14, wherein the insert includes a channel configured to receive a screw and wherein the intramedullary rod includes a threaded channel configured to receive the screw.

16. The intramedullary rod kit of claim 15, wherein the threaded channel further comprises an opening extending through the intramedullary rod and configured to receive the shaft.

17. The intramedullary rod kit of claim 1, wherein the first mounting section comprises at least one channel having a threaded inner diameter.

18. The intramedullary rod kit of claim 17, further comprising at least one bone screw configured to be passed through the first mounting section to mount the intramedullary rod to a diaphyseal portion of the radius.

19. The intramedullary rod kit of claim 18, wherein the bone screw is a unicortical bone screw or a bicortical bone screw.

20. The intramedullary rod kit of claim 1, wherein the joint segment includes an opening into a longitudinal channel that extends along a portion of a length of the intramedullary rod.

21. The intramedullary rod kit of claim 20, wherein the longitudinal channel includes a threaded portion.

22. The intramedullary rod kit of claim 20, further comprising a guide configured to be mounted to the intramedullary rod and configured to orient drill guides to be collinear with the first mounting section and the second mounting section of the intramedullary rod.

23. The intramedullary rod kit of claim 22, wherein the guide is mounted to the intramedullary rod by insertion of a portion of the guide into the longitudinal channel in the intramedullary rod.

24. The intramedullary rod kit of claim 23, wherein the portion of the guide that is inserted into the longitudinal channel is threadably inserted into the longitudinal channel.

25. An intramedullary rod kit for fixation of a distal radius fracture, the intramedullary rod kit comprising:
an intramedullary rod comprising:
a diaphyseal segment including at least one first mounting section configured to receive a tensioning device,
a middle segment; and
a joint segment including at least one second mounting section configured to receive a tine,
wherein the diaphyseal segment, the middle segment, and the joint segment define a curved configuration that is substantially similar to a curvature of the intramedullary canal of a human radius; and
at least one tine, wherein the tine is a snap fit tine including a head having an opening into which teeth protrude and from which a shaft extends and wherein the second mounting section includes a channel around at least a portion of the circumference of the intramedullary rod and from which teeth protrude and wherein the head is configured to be mated with the second mounting section.

26. The intramedullary rod kit of claim 25, wherein an outer diameter of the intramedullary rod varies between approximately 10 mm and 25 mm at the joint segment and approximately 2 mm and 9 mm at the diaphyseal segment.

27. The intramedullary rod kit of claim 25, wherein an outer diameter of the intramedullary rod varies between approximately 12 mm and 15 mm at the joint segment and approximately 3 mm and 5 mm at the diaphyseal segment.

28. The intramedullary rod kit of claim 25, wherein an outer diameter of the intramedullary rod varies between approximately 14 mm at the joint segment and approximately 3 mm at the diaphyseal segment.

29. The intramedullary rod kit of claim 25, wherein the joint segment has a round cross-section or an oval cross-section.

30. The intramedullary rod kit of claim 25, wherein the diaphyseal segment has a round or a generally round cross-section.

31. The intramedullary rod kit of claim 25, wherein a length of the rod is between approximately 50 mm and 100 mm.

32. The intramedullary rod kit of claim 25, wherein a length of the rod is approximately 80 mm.

33. The intramedullary rod kit of claim 25, further comprising written instructions for use.

34. The intramedullary rod kit of claim 25, further comprising an instructional video.

35. The intramedullary rod kit of claim 25, further comprising a drill bit configured to drill a hole in bone tissue.

36. The intramedullary rod kit of claim 25, wherein the diaphyseal segment of the intramedullary rod comprises a dimpled surface.

37. The intramedullary rod kit of claim 25, wherein the intramedullary rod, and/or the tine are coated with a therapeutic agent.

38. The intramedullary rod kit of claim 25, wherein the first mounting section comprises at least one channel having a threaded inner diameter.

39. The intramedullary rod kit of claim 38, further comprising at least one bone screw configured to be passed through the first mounting section to mount the intramedullary rod to a diaphyseal portion of the radius.

40. The intramedullary rod kit of claim 39, wherein the bone screw is a unicortical bone screw or a bicortical bone screw.

41. The intramedullary rod kit of claim 25, wherein the joint segment includes an opening into a longitudinal channel that extends along a portion of a length of the intramedullary rod.

42. The intramedullary rod kit of claim 41, wherein the longitudinal channel includes a threaded portion.

43. The intramedullary rod kit of claim 41, further comprising a guide configured to be mounted to the intramedullary rod and configured to orient drill guides to be collinear with the first mounting section and the second mounting section of the intramedullary rod.

44. The intramedullary rod kit of claim 43, wherein the guide is mounted to the intramedullary rod by insertion of a portion of the guide into the longitudinal channel in the intramedullary rod.

45. The intramedullary rod kit of claim 44, wherein the portion of the guide that is inserted into the longitudinal channel is threadably inserted into the longitudinal channel.

46. An intramedullary rod kit for fixation of a distal radius fracture, the intramedullary rod kit comprising:
an intramedullary rod comprising:
a diaphyseal segment including at least one first mounting section configured to receive a tensioning device,
a middle segment; and
a joint segment including at least one second mounting section configured to receive a tine,
wherein the diaphyseal segment, the middle segment, and the joint segment define a curved configuration that is substantially similar to a curvature of the intramedullary canal of a human radius;
at least one tine; and
a tensiometer mounted to one or more of the intramedullary rod and the tine and being configured to measure a tension exerted against one or both of the intramedullary rod and the tine.

47. The intramedullary rod kit of claim 46, further comprising:
a transmitter for transmitting the measured tension; and
a receiver for receiving and displaying the measured tension.

48. The intramedullary rod kit of claim 46, wherein an outer diameter of the intramedullary rod varies between approximately 10 mm and 25 mm at the joint segment and approximately 2 mm and 9 mm at the diaphyseal segment.

49. The intramedullary rod kit of claim 46, wherein an outer diameter of the intramedullary rod varies between approximately 12 mm and 15 mm at the joint segment and approximately 3 mm and 5 mm at the diaphyseal segment.

50. The intramedullary rod kit of claim 46, wherein an outer diameter of the intramedullary rod varies between approximately 14 mm at the joint segment and approximately 3 mm at the diaphyseal segment.

51. The intramedullary rod kit of claim 46, wherein the joint segment has one of a round cross-section and or an oval cross-section.

52. The intramedullary rod kit of claim 46, wherein the diaphyseal segment has a round or a generally round cross-section.

53. The intramedullary rod kit of claim 46, wherein a length of the rod is between approximately 50 mm and 100 mm.

54. The intramedullary rod kit of claim 46, wherein a length of the rod is approximately 80 mm.

55. The intramedullary rod kit of claim 46, further comprising written instructions for use.

56. The intramedullary rod kit of claim 46, further comprising an instructional video.

57. The intramedullary rod kit of claim 46, further comprising a drill bit configured to drill a hole in bone tissue.

58. The intramedullary rod kit of claim 46, wherein the diaphyseal segment of the intramedullary rod comprises a dimpled surface.

59. The intramedullary rod kit of claim 46, wherein the intramedullary rod, and/or the tine are coated with a therapeutic agent.

60. The intramedullary rod kit of claim 46, wherein the tine comprises a press-fit tine including a head from which a shaft extends, wherein the shaft includes a stop, wherein the head and stop are configured to be mated with the second mounting section.

61. The intramedullary rod kit of claim 46, wherein the first mounting section comprises at least one channel having a threaded inner diameter.

62. The intramedullary rod kit of claim 61, further comprising at least one bone screw configured to be passed through the first mounting section to mount the intramedullary rod to a diaphyseal portion of the radius.

63. The intramedullary rod kit of claim 62, wherein the bone screw is a unicortical bone screw or a bicortical bone screw.

64. The intramedullary rod kit of claim 46, wherein the joint segment includes an opening into a longitudinal channel that extends along a portion of a length of the intramedullary rod.

65. The intramedullary rod kit of claim 64, wherein the longitudinal channel includes a threaded portion.

66. The intramedullary rod kit of claim 64, further comprising a guide configured to be mounted to the intramedullary rod and configured to orient drill guides to be collinear with the first mounting section and the second mounting section of the intramedullary rod.

67. The intramedullary rod kit of claim 66, wherein the guide is mounted to the intramedullary rod by insertion of a portion of the guide into the longitudinal channel in the intramedullary rod.

68. The intramedullary rod kit of claim 67, wherein the portion of the guide that is inserted into the longitudinal channel is threadably inserted into the longitudinal channel.

69. The intramedullary rod kit of claim 46, wherein the tine comprises a shaft and is mounted to the rod in the second mounting section.

70. The intramedullary rod kit of claim 69, wherein the second mounting section comprises a channel that includes a threaded portion and wherein the tine includes a first non-threaded section and a second threaded section, wherein the second threaded section is configured to be threadably mated to the threaded portion of the channel.

71. The intramedullary rod kit of claim 69, wherein the second mounting section comprises a channel that includes a threaded portion and wherein the tine includes a first threaded section and a second threaded section, wherein the second threaded section is configured to be threadably mated to the threaded portion of the channel.

72. The intramedullary rod kit of claim 71, wherein the first threaded section includes threads that are configured to be threadably mated with the bone fragment.

73. An intramedullary rod kit for fixation of a distal radius fracture, the intramedullary rod kit comprising:
an intramedullary rod comprising:
a diaphyseal segment including at least one first mounting section configured to receive a tensioning device,
a middle segment; and
a joint segment including at least one second mounting section configured to receive a tine,
wherein the diaphyseal segment, the middle segment, and the joint segment define a curved configuration that is substantially similar to a curvature of the intramedullary canal of a human radius;
at least one tine; and
a tensioning device, wherein the tensioning device comprises a tie band fastener including a tie band, a slidable tab, and a stop.

74. The intramedullary rod kit of claim 73, wherein an outer diameter of the intramedullary rod varies between approximately 10 mm and 25 mm at the joint segment and approximately 2 mm and 9 mm at the diaphyseal segment.

75. The intramedullary rod kit of claim 73, wherein an outer diameter of the intramedullary rod varies between approximately 12 mm and 15 mm at the joint segment and approximately 3 mm and 5 mm at the diaphyseal segment.

76. The intramedullary rod kit of claim 73, wherein an outer diameter of the intramedullary rod varies between approximately 14 mm at the joint segment and approximately 3 mm at the diaphyseal segment.

77. The intramedullary rod kit of claim 73, wherein the joint segment has one of a round cross-section and or an oval cross-section.

78. The intramedullary rod kit of claim 73, wherein the diaphyseal segment has a round or a generally round cross-section.

79. The intramedullary rod kit of claim 73, wherein a length of the rod is between approximately 50 mm and 100 mm.

80. The intramedullary rod kit of claim 73, wherein a length of the rod is approximately 80 mm.

81. The intramedullary rod kit of claim 73, further comprising written instructions for use.

82. The intramedullary rod kit of claim 73, further comprising an instructional video.

83. The intramedullary rod kit of claim 73, further comprising a drill bit configured to drill a hole in bone tissue.

84. The intramedullary rod kit of claim 73, wherein the diaphyseal segment of the intramedullary rod comprises a dimpled surface.

85. The intramedullary rod kit of claim 73, wherein the intramedullary rod, and/or the tine are coated with a therapeutic agent.

86. The intramedullary rod kit of claim 73, wherein the tine comprises a press-fit tine including a head from which a shaft extends, wherein the shaft includes a stop, wherein the head and stop are configured to be mated with the second mounting section.

87. The intramedullary rod kit of claim 73, wherein the first mounting section comprises at least one channel having a threaded inner diameter.

88. The intramedullary rod kit of claim 87, further comprising at least one bone screw configured to be passed through the first mounting section to mount the intramedullary rod to a diaphyseal portion of the radius.

89. The intramedullary rod kit of claim 88, wherein the bone screw is a unicortical bone screw or a bicortical bone screw.

90. The intramedullary rod kit of claim 73, wherein the joint segment includes an opening into a longitudinal channel that extends along a portion of a length of the intramedullary rod.

91. The intramedullary rod kit of claim 90, wherein the longitudinal channel includes a threaded portion.

92. The intramedullary rod kit of claim 90, further comprising a guide configured to be mounted to the intramedullary rod and configured to orient drill guides to be collinear with the first mounting section and the second mounting section of the intramedullary rod.

93. The intramedullary rod kit of claim 92, wherein the guide is mounted to the intramedullary rod by insertion of a portion of the guide into the longitudinal channel in the intramedullary rod.

94. The intramedullary rod kit of claim 93, wherein the portion of the guide that is inserted into the longitudinal channel is threadably inserted into the longitudinal channel.

95. The intramedullary rod kit of claim 73, wherein the tine comprises a shaft and is mounted to the rod in the second mounting section.

96. The intramedullary rod kit of claim 95, wherein the second mounting section comprises a channel that includes a threaded portion and wherein the tine includes a first non-threaded section and a second threaded section, wherein the second threaded section is configured to be threadably mated to the threaded portion of the channel.

97. The intramedullary rod kit of claim 95, wherein the second mounting section comprises a channel that includes a threaded portion and wherein the tine includes a first threaded section and a second threaded section, wherein the second threaded section is configured to be threadably mated to the threaded portion of the channel.

98. The intramedullary rod kit of claim 97, wherein the first threaded section includes threads that are configured to be threadably mated with the bone fragment.

99. An intramedullary rod kit for fixation of a distal radius fracture, the intramedullary rod kit comprising:
an intramedullary rod comprising:
a diaphyseal segment including at least one first mounting section configured to receive a tensioning device,
a middle segment; and
a joint segment including at least one second mounting section configured to receive a tine,
wherein the diaphyseal segment, the middle segment, and the joint segment define a curved configuration that is substantially similar to a curvature of the intramedullary canal of a human radius;
at least one tine; and
a tensioning device, wherein the tensioning device comprises a molly bolt system that includes a head, a nut, and one or more flexible arms extending between the head and the nut.

100. The intramedullary rod kit of claim 99, wherein an outer diameter of the intramedullary rod varies between approximately 10 mm and 25 mm at the joint segment and approximately 2 mm and 9 mm at the diaphyseal segment.

101. The intramedullary rod kit of claim 99, wherein an outer diameter of the intramedullary rod varies between approximately 12 mm and 15 mm at the joint segment and approximately 3 mm and 5 mm at the diaphyseal segment.

102. The intramedullary rod kit of claim 99, wherein an outer diameter of the intramedullary rod varies between approximately 14 mm at the joint segment and approximately 3 mm at the diaphyseal segment.

103. The intramedullary rod kit of claim 99, wherein the joint segment has one of a round cross-section and or an oval cross-section.

104. The intramedullary rod kit of claim 99, wherein the diaphyseal segment has a round or a generally round cross-section.

105. The intramedullary rod kit of claim 99, wherein a length of the rod is between approximately 50 mm and 100 mm.

106. The intramedullary rod kit of claim 99, wherein a length of the rod is approximately 80 mm.

107. The intramedullary rod kit of claim 99, further comprising written instructions for use.

108. The intramedullary rod kit of claim 99, further comprising an instructional video.

109. The intramedullary rod kit of claim 99, further comprising a drill bit configured to drill a hole in bone tissue.

110. The intramedullary rod kit of claim 99, wherein the diaphyseal segment of the intramedullary rod comprises a dimpled surface.

111. The intramedullary rod kit of claim 99, wherein the intramedullary rod, and/or the tine are coated with a therapeutic agent.

112. The intramedullary rod kit of claim 99, wherein the tine comprises a press-fit tine including a head from which a shaft extends, wherein the shaft includes a stop, wherein the head and stop are configured to be mated with the second mounting section.

113. The intramedullary rod kit of claim 99, wherein the first mounting section comprises at least one channel having a threaded inner diameter.

114. The intramedullary rod kit of claim 113, further comprising at least one bone screw configured to be passed through the first mounting section to mount the intramedullary rod to a diaphyseal portion of the radius.

115. The intramedullary rod kit of claim 114, wherein the bone screw is a unicortical bone screw or a bicortical bone screw.

116. The intramedullary rod kit of claim 99, wherein the joint segment includes an opening into a longitudinal channel that extends along a portion of a length of the intramedullary rod.

117. The intramedullary rod kit of claim 116, wherein the longitudinal channel includes a threaded portion.

118. The intramedullary rod kit of claim 116, further comprising a guide configured to be mounted to the intramedullary rod and configured to orient drill guides to be collinear with the first mounting section and the second mounting section of the intramedullary rod.

119. The intramedullary rod kit of claim 118, wherein the guide is mounted to the intramedullary rod by insertion of a portion of the guide into the longitudinal channel in the intramedullary rod.

120. The intramedullary rod kit of claim 119, wherein the portion of the guide that is inserted into the longitudinal channel is threadably inserted into the longitudinal channel.

121. The intramedullary rod kit of claim 99, wherein the tine comprises a shaft and is mounted to the rod in the second mounting section.

122. The intramedullary rod kit of claim 121, wherein the second mounting section comprises a channel that includes a threaded portion and wherein the tine includes a first non-threaded section and a second threaded section, wherein the second threaded section is configured to be threadably mated to the threaded portion of the channel.

123. The intramedullary rod kit of claim 121, wherein the second mounting section comprises a channel that includes a threaded portion and wherein the tine includes a first threaded section end a second threaded section, wherein the second threaded section is configured to be threadably mated to the threaded portion of the channel.

124. The intramedullary rod kit of claim 123, wherein the first threaded section includes threads that are configured to be threadably mated with the bone fragment.

* * * * *